(12) United States Patent
Ellman

(10) Patent No.: US 8,409,194 B1
(45) Date of Patent: Apr. 2, 2013

(54) RF INTERVERTEBRAL DISC SURGICAL SYSTEM

(76) Inventor: Alan Ellman, Baldwin, NY (US)

( * ) Notice: Subject to any disclaimer, the term of this patent is extended or adjusted under 35 U.S.C. 154(b) by 0 days.

(21) Appl. No.: 13/135,343

(22) Filed: Jul. 5, 2011

Related U.S. Application Data

(62) Division of application No. 12/220,187, filed on Jul. 23, 2008.

(51) Int. Cl.
*A61B 18/14* (2006.01)

(52) U.S. Cl. ............... 606/41; 606/46; 607/99; 607/117

(58) Field of Classification Search ............. 606/32–34, 606/46, 41; 607/99, 117
See application file for complete search history.

(56) References Cited

U.S. PATENT DOCUMENTS

| | | | | |
|---|---|---|---|---|
| 5,242,439 | A * | 9/1993 | Larsen et al. | 606/15 |
| 6,468,274 | B1 * | 10/2002 | Alleyne et al. | 606/41 |
| 6,512,958 | B1 * | 1/2003 | Swoyer et al. | 607/117 |
| 6,971,393 | B1 * | 12/2005 | Mamo et al. | 128/898 |
| 2004/0116977 | A1 * | 6/2004 | Finch et al. | 607/46 |
| 2004/0193151 | A1 * | 9/2004 | To et al. | 606/41 |
| 2006/0149279 | A1 * | 7/2006 | Mathews | 606/90 |

\* cited by examiner

*Primary Examiner* — Michael Peffley
*Assistant Examiner* — Thomas Giuliani

(57) ABSTRACT

A spinal surgical system comprising a plurality of surgical components for cooperating with a electrosurgical handpiece comprising an elongated tubular member housing an electrode, with the tubular member configured to fit within and be extended down a standard sized cannula in a MIS procedure. The system components comprise one or more cannulas, straight or beveled; one or more guide wires, with and without pointed ends for piercing tissue; a tapered dilator; a trephine; and one or more depth control stops for mounting on the cannula for monitoring its depth. The system is especially useful for performing a discectomy.

12 Claims, 4 Drawing Sheets

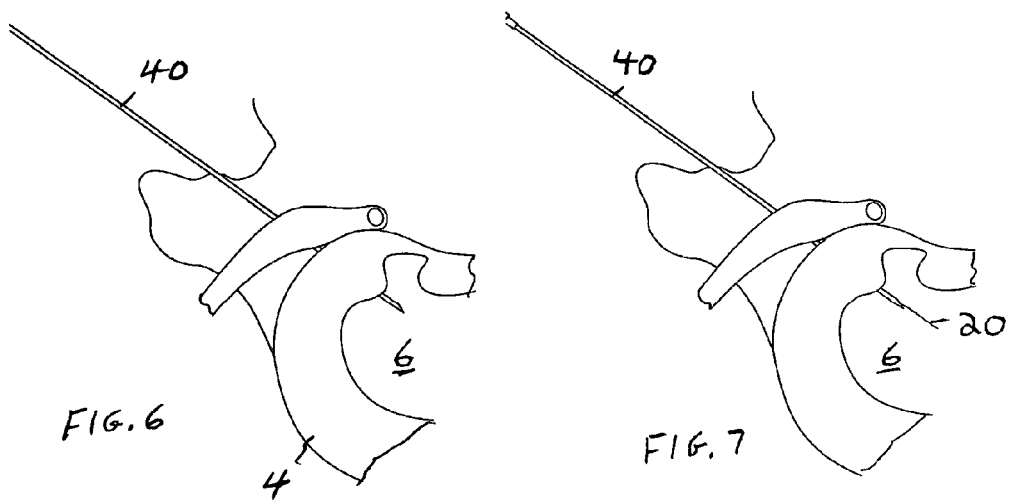
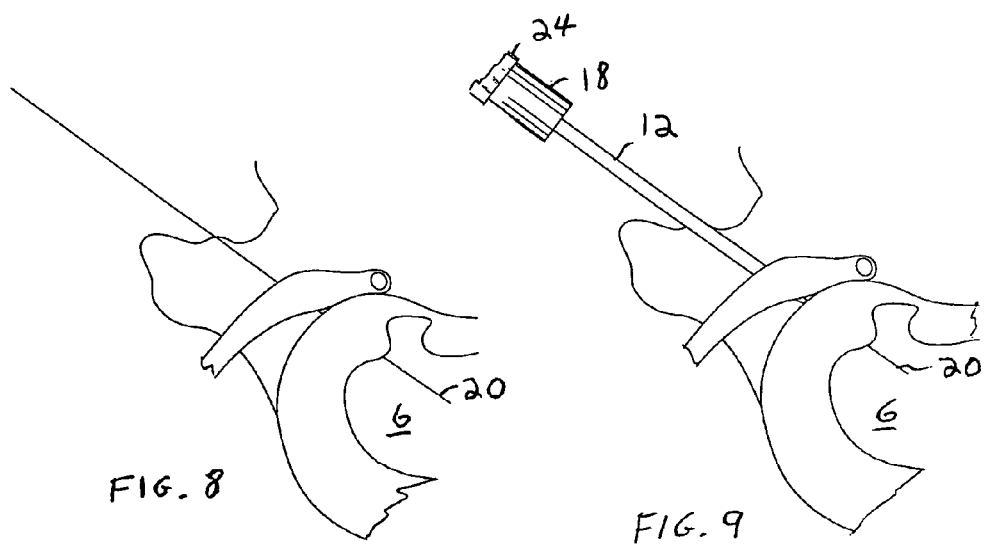

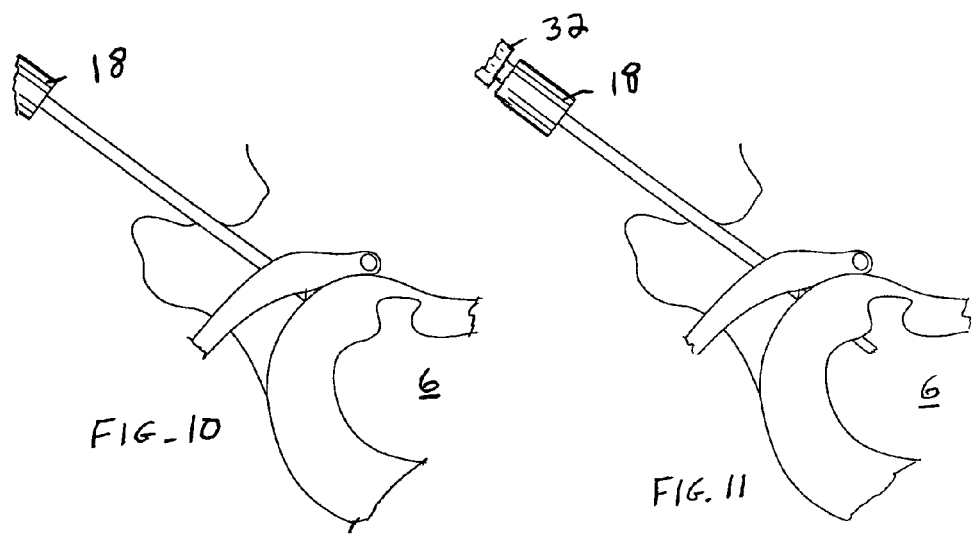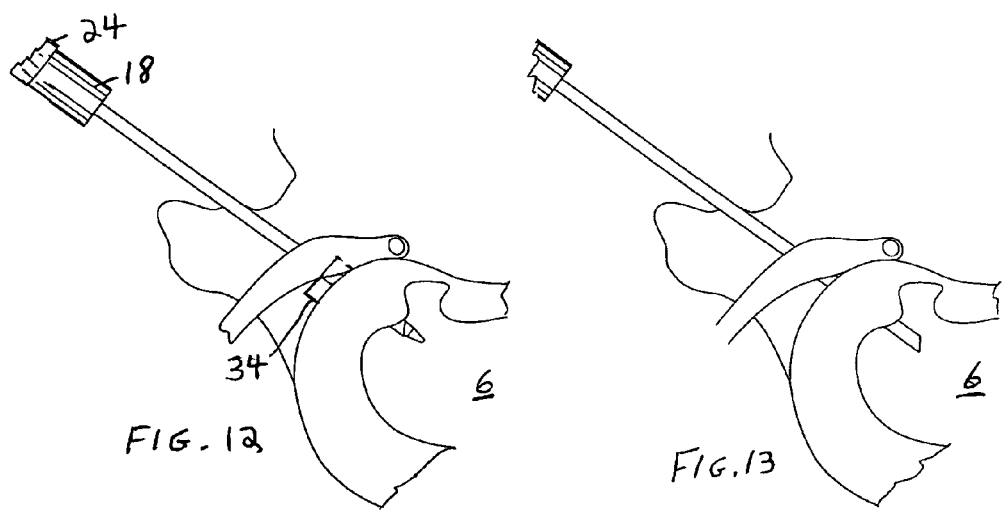

RF INTERVERTEBRAL DISC SURGICAL SYSTEM

This application is a division of prior patent application AN 12/220,187, filed Jul. 23, 2008.

This invention relates to an intervertebral disc surgical system, and in particular to such a system employing electrosurgery for performing spinal and related surgical procedures.

BACKGROUND OF THE INVENTION

Our earlier U.S. Pat. No. 7,137,982, the contents of which are herein incorporated by reference, describes an electrosurgical instrument for spinal procedures comprising a generally scoop-shaped cup whose periphery is electrically active and is capable of applying RF electrosurgical currents to spinal tissue.

While the patented device as explained in that patent is suitable for many spinal procedures, there is a need in the art for other instruments that can electrosurgically remove or shrink tissue, and specifically disc nucleus pulposus, via a cannula for minimally invasive surgical (MIS) procedures, such as a discectomy.

SUMMARY OF THE INVENTION

An object of the invention is an improved surgical system for performing an MIS discectomy procedure.

Another object of the invention is an improved procedure for producing a void or cavity in or reduction of human tissue, especially in the spinal region.

In accordance with one aspect of our invention, our novel system comprises a plurality of surgical components for cooperating with an electrosurgical handpiece of the type comprising an elongated tubular member housing an electrode, with the tubular member configured to fit within and be extended down a standard sized cannula in a MIS procedure. The system components comprise one or more cannulas, straight or beveled; one or more guide wires, with and without pointed ends for piercing tissue; a tapered dilator; a trephine; and a depth control stop for mounting on the cannula for monitoring its depth in the patient's tissue.

The electrosurgical handpiece typically comprises a proximal end including a handle for the surgeon and may be supplied with fittings for connection to a source of irrigation fluid and a source of suction. The distal end of the instrument has an active end that may comprise a slightly flexible curved wire or straight electrode, typically bipolar. The tubular member of the handpiece may be rigid or flexible.

The system components are designed to provide targeted access via one of the cannulas, during say a discectomy, to the disc annulus by the active end of the electrosurgical handpiece which when energized can provide tissue debulking, ablation or modulation, as desired. Put another way, the use of the components, as described below, can provide precise placement and control of the electrosurgical electrode providing exact pathology treatment.

Preferably, the far end of the handpiece tubular member is constructed of a radio-opaque material such that the instrument end is visible during fluoroscopic examination while the procedure is carried out.

The housed wire electrode is electrically active and is capable when energized of applying electrosurgical currents to human tissue with the result that a void or cavity or tunnel can be formed in the tissue to a considerable depth. The tissue removed to form the cavity may then be easily aspirated via the suction port.

Preferably, radio-frequency (RF) electrosurgical currents, in a frequency range preferably above 3 MHz, with 4 MHz being preferred, are employed. It is believed that 4 MHz radiofrequency energy has been proven to be a self-limiting, minimal penetration energy source capable of precise tissue interaction. Thus, electrosurgical instruments that emit 4 MHz radiofrequency currents will be attractive to spinal surgeons needing to produce a space-specific nucleotomy efficiently and safely. In combination with the innovative RF delivery system in a MIS procedure, radiofrequency energy can result in precision extraction of the nucleus pulposus and/or the entire disc that will enable a void to be created that will accommodate a replacement substance or device. Since lateral heat is typically not a byproduct of 4 MHz RF currents, damage to endplates can be minimized or avoided, nor will the RF currents violate the annulus.

Thus, a MIS electrosurgical procedure using the novel system components described herein enables physicians to offer to patients a treatment that is efficiently performed, relatively easily learned and thus performed at a significantly reduced price, and with less tissue damage and superior results compared to procedures done with other voiding devices.

The system of the invention is especially valuable for treating patients with contained intravertebral disc herniations or bulges.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals or letters signifying the same or similar components.

BRIEF DESCRIPTION OF THE DRAWINGS

FIGS. 6-17 are schematic views illustrating different steps in a surgical procedure using the surgical system of FIG. 1.

DETAILED DESCRIPTION OF THE PREFERRED EMBODIMENTS

Figure 1:
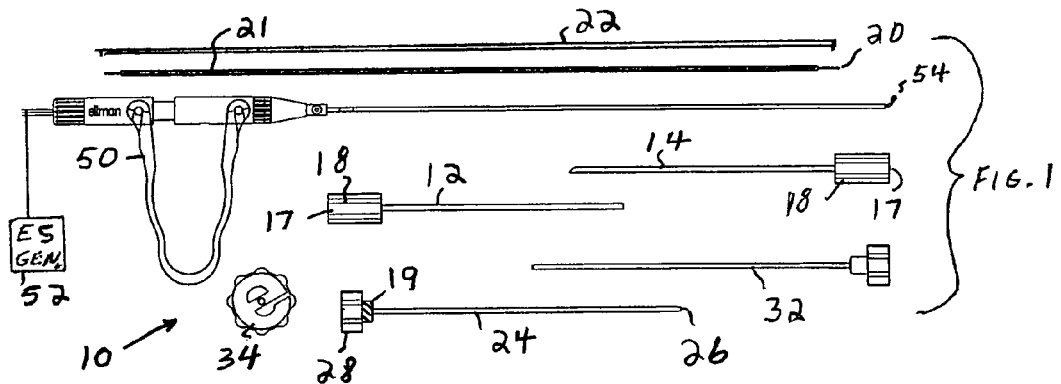
FIG. 1 is a plan view of the components of one form of surgical system of the invention, the system in this case being shown with an electrosurgical handpiece shown schematically connected to an electrosurgical generator.
Figure 5:
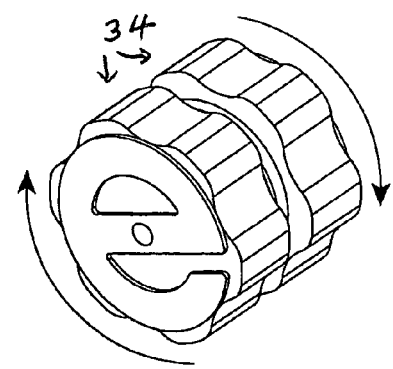
FIG. 5 illustrates operation of depth stop for use in the surgical system of FIG. 1.
Figure 14:
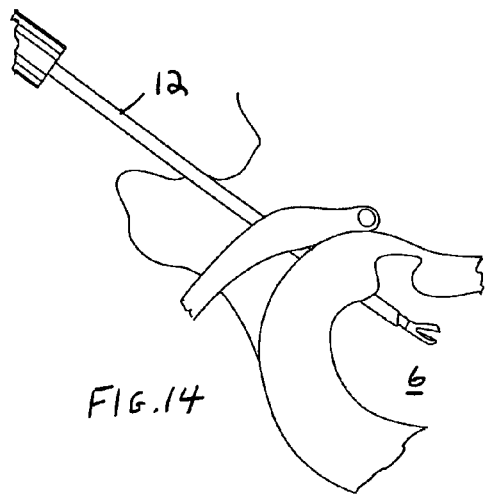
Figure 15:
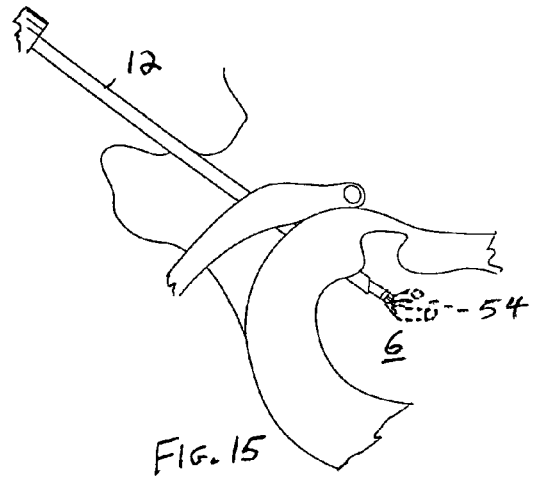

FIG. 1 illustrates the components for one form of discectomy system 10 in accordance with the invention. It comprises one or more cannulas, in this instance one 12 with a straight end and one 14 with a beveled end. Each cannula comprises an elongated straight tube, about 3.4 mm in outer diameter, length about 16.5 cm connected to a cannula head 18. The free end of the cannula head 18 has an internally-threaded opening 17. A common bore or lumen typically of about 3 mm extends through the tube and head. Two guide wires are provided, one small 20 in a removable plastic tube 21 and one large 22. Each guide wire is solid with an outer diameter of 1 and 1.3 mm respectively, about 40 cm long. Each guide wire preferably has pointed ends for piercing tissue. A dilator 24 is provided with a tapered tip 26 and a dilator head 28 with a forwardly projecting threaded end 19 for removable connection to the backward extended threaded opening 17 in the cannula head. When threaded together, a cannula and the dilator can be operated together as a single unit, or separated can operate as separate units. The system also comprises a trephine 32 having a straight tube terminating in a beveled cutting edge. The dilator has an OD of about 2.8 mm tapering down to about 2.2 mm. The trephine has about the same OD. Their lengths are about 19.5 cm. A depth control stop is shown at 34 for mounting on the cannula for monitoring its depth in the tissue. The depth stop comprises two threaded parts (see FIG. 5) that can separate when on the cannula to adjust their position on the cannula, and when tightened will lock to the cannula.

One procedure in accordance with the invention using these components is now described in connection with FIGS. 6-17 which show schematically a patient's back with a spinal disc comprising an annulus 4 surrounding the nucleus pulposus 6.

Figure 2:
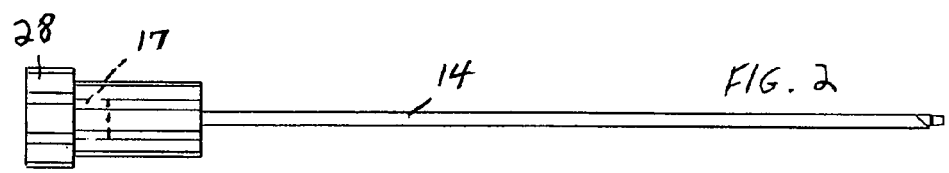
FIG. 2 is a plan view of a dilator assembled to a cannula of the surgical system of FIG. 1.
Figure 3:
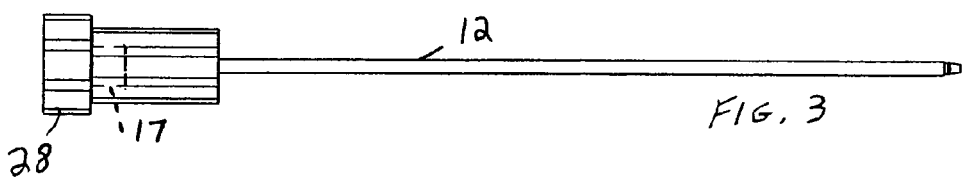
FIG. 3 is a plan view of a dilator assembled to a different cannula of the surgical system of FIG. 1.
Figure 16:
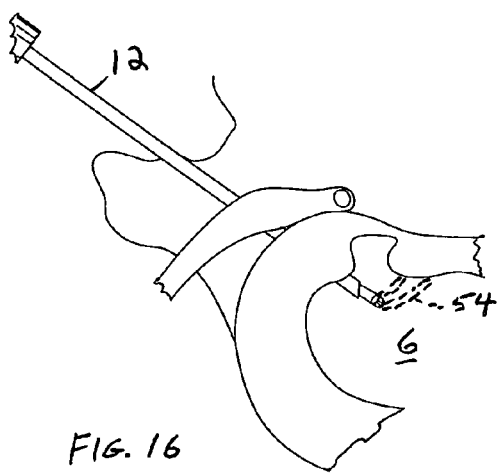
Figure 17:
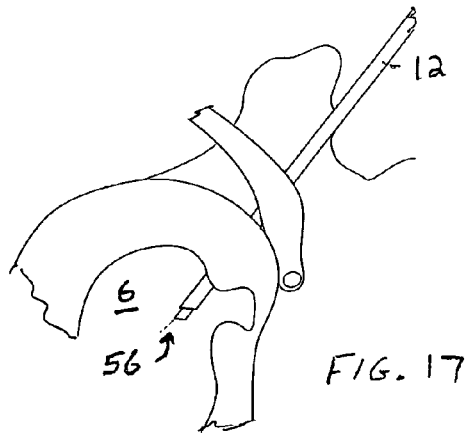

The patient may be positioned on a radiolucent table on a curved spinal frame in prone position, the lumbar spine area prepped and draped in the usual sterile fashion, and the entry site marked, using, for example, a sterile marking pen 8-10 cm from midline on the affected side using fluoroscopic guidance. The skin is then anesthetized with local anesthetic using a 25-gauge needle. A standard 18-gauge, 8-inch long spinal needle 40 is inserted through the marked entry point at a 45-degree angle to the skin (FIG. 6). The needle is advanced toward the foramen while the position is checked using both anterior/posterior (AP) and lateral fluoroscopy. The needle is then advanced into the disc using standard discography technique. The final position is verified using fluoroscopy. Discography is performed using 3 cc of contrast dye containing antibiotics and indigo carmine. The discogram is performed to verify concordant pain and visualize disc morphology. One of the guide wires 20 (FIG. 7) is threaded through the lumen of the needle 40 into the disc nucleus 6. Two different sizes of guide wires are provided for use with spinal needles with different sized lumens. A 3-4 mm skin incision is made at the needle site using a #11 scalpel. The needle 40 is subsequently removed leaving the guide wire 20 in place (FIG. 8). The working cannula 12 and dilator 24 joined together are placed over the guide wire 20 and advanced toward the annulus (FIG. 9). FIGS. 2 and 3 show a dilator 28 screwed and assembled to the head of a cannula 12, 14. The respective lengths are such that the tapered end 26 of the dilator protrudes about 4 mm from the free end of the cannula. The dilator 24 (FIG. 10) is removed from the working cannula 12. The trephine 32 (FIG. 11) is inserted through the cannula 12 and advanced toward the outer surface of the disc annulus. The trephine protrudes about 1 cm from the free end of the cannula An annulotomy is created by applying slight pressure and a 360 degree rotation of the trephine 1-3 turns. The trephine 32 is then removed and replaced by the dilator 24. The cannula 12 with dilator 24 is advanced under fluoroscopic guidance into the nucleus (FIG. 12). When the dilator 24 is then removed, a portal into the disc is created (FIG. 13). The depth stop 34 (shown only in FIG. 12) mounted on the cannula 12 is advanced to the patient's skin and secured to the cannula to prevent advancement. A standard 2.5 mm diameter endoscopic grasping forceps (FIG. 14) can be used to manually extract nucleus material. A bipolar electrosurgical handpiece 50 as described in U.S. Pat. Nos. 6,231,571 and D562,978, the contents of which are herein incorporated by reference, an example of which is known commercially as the Trigger-Flex Bipolar System and available from Elliquence LLC of Oceanside, N.Y., is connected to an RF electrosurgical generator 52, also available commercially from Elliquence LLC of Oceanside, N.Y. set to a relatively low power in the bipolar HEMO mode. The electrosurgical handpiece 50 may be included in the package with the other components or provided separately. The lowest power setting to achieve desired tissue effect should be used. The RF energy is activated using footswitch activation while the handle is squeezed to extend and retract the electrode (FIG. 15), the active bendable electrode end 54 being deployed and retracted into the nucleus to create tracks of nucleus removal. Preferably, the electrode tracks are directed into the 11:, 12:, 1:, 5:, 6: and 7: o'clock positions in order to accomplish nucleus pulposus decompression. At a lower power setting, an annuloplasty can be performed at the annulus (FIG. 16). The electrosurgical handpiece is extracted from the cannula at the conclusion of the procedure. While stabilizing the skin around the cannula with the fingers of one hand, the other hand should slowly withdraw the cannula and dilator together if added. 2-3 sutures are used to close the surgical site and a sterile bandage applied. The patient is provided with post-procedural instructions. FIG. 17 illustrates while the cannula is still in position that suction 56 can be provided to extract tissue.

Certain cautions are advisable. The procedure may be performed under local anesthesia and/or conscious sedation to allow for patient monitoring for signs of nerve root irritation. Continuous fluoroscopic imaging in A/P and lateral views should be performed throughout the procedure to verify device positioning. Irrigation should be permitted to flow continuously during the procedure to ensure proper cooling of the disc space. Care should be taken to make certain that the active electrode remains within the confines of the disc during activation.

Either the small guide wire or the large guide wire is inserted directly through the musculature toward the symptomatic disc. Once the guide wire is in the correct position within the disc, the chosen cannula and the tapered dilator, completely attached via the threaded proximal head, is inserted. See FIG. 6 for component orientation. The depth stop 54 can be added to the selected cannula in the open depth stop position by counter-rotation of its two ends. After positioning upon cannula shaft, it is secured by rotation of its ends in opposite directions. See FIG. 5. The cannula and tapered dilator are passed together over the guide wire and inserted down to the annulus, whereupon the tapered dilator is removed from the cannula.

Figure 4:
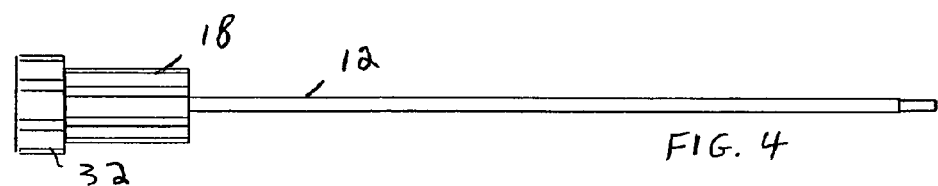
FIG. 4 is a plan view of a trephine assembled to a cannula of the surgical system of FIG. 1.

Performing an annulotomy with the trephine is relatively straightforward. To incise the annulus, the trephine 32 is placed over the guide wire and extended through the cannula 12. See FIG. 4. The trephine should be rotated with light pressure in a clockwise motion to incise the annulus. Once the incision is made, the trephine and guide wire are removed from the cannula and the cannula is advanced into the disc nucleus. The depth stop should be used and secured at the patient's skin upon the cannula shaft to prevent inadvertent advancement, even though with continuous fluoroscopic monitoring.

With the cannula confirmed in optimum position, the cannula is in place to perform a discectomy procedure.

The RF electrosurgical handpiece called Trigger-Flex System has on its shaft two etched markings (not shown) near the handle to aid in surgical depth monitoring:

Position 1: When the proximal (top) of the cannula head is flush to the distal etched marking, the cannula tip will be flush to the Trigger-Flex shaft.

Position 2: When the proximal (top) of the cannula head is flush to the proximal etched marking, the Trigger-Flex shaft will be exposed 1.0 cm beyond the cannula tip.

Position 3: When the proximal (top) of the cannula head is flush to the distal edge of the Trigger-Flex handle, the Trigger-Flex shaft will be exposed 3.3 cm beyond the cannula tip. The shaft has an overall length of about 23 cm and an OD of about 2.3 mm.

To perform nucleoplasty, with the Trigger-Flex System in position at or in the nucleus, the handle is squeezed for full electrode advancement then retraction. This technique should be repeated for at least 5 passes in the disc while rotating the device. For annuloplasty; the Trigger-Flex System should be directed toward the inner annular wall in a sweeping motion.

While the Trigger-Flex System is preferred, other elongated electrosurgical handpieces can be substituted.

While the instrument of the invention is especially useful for spinal procedures, it is not limited to such uses and it will be understood that it can be employed in any electrosurgical procedure employing a cannula in MIS.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A spinal procedure comprising the steps:
   a. providing a cannula, a guide wire, a tapered dilator with a lumen, a trephine with a lumen, a depth control stop, and an elongated electrosurgical instrument that can be activated to generate electrosurgical currents,
   b. positioning a patent in a prone position,
   c. subjecting the patient to conscious sedation,
   d. a spinal needle with a lumen is inserted into the patient's back 8-10 cm from midline toward a spinal disc comprising an annulus surrounding a nucleus pulposus and through an intervertebral foramen, a guide wire is then threaded through the needle lumen into the disc nucleus,
   e. a 3-4 mm skin incision is made at the needle site and the spinal needle is then removed leaving the guide wire in place,
   f. the cannula and dilator joined together are then placed over the guide wire and advanced toward the annulus,
   g. the cannula with dilator is advanced under fluoroscopic guidance into the nucleus,
   h. next the dilator is removed creating a portal into the disc,
   i. next the depth control stop is mounted on the cannula and advanced to the patient's skin and secured to prevent advancement of the cannula,
   j. next the electrosurgical instrument is advanced through the cannula and into the pulposus and activated to generate electrosurgical currents to remove, shrink or modulate pulposus or annulus tissue.

2. A procedure as set forth in claim 1, further comprising: k. after step f. and before step g., the dilator is removed from the cannula, l. the trephine is inserted through the cannula and advanced toward the outer surface of the disc annulus and an annulotomy is created by rotation of the trephine 1-3 turns, m. following step l, the trephine is removed and replaced by the dilator.

3. The procedure of claim 2, wherein the electrosurgical instrument is activated with high frequency electrosurgical currents at a frequency of about 4 MHz.

4. A spinal procedure comprising the steps:
   (a) providing a packaged MIS intervertebral disc surgical system comprising:
      (i) one or more straight or beveled cannulas each having an outside diameter of about 3.4 mm and each having a proximal and distal end, the cannulas configured with a lumen to receive an elongated tubular member of an electrosurgical instrument,
      (ii) one or more guide wires, at least one of the guide wires having a pointed end for piercing tissue, each of the guide wires being configured to fit within each of the cannula's lumen so that a cannula can be advanced into tissue guided by an introduced guide wire,
      (iii) a tapered dilator configured to slide over a guide wire,
      (iv) a trephine configured to slide over a guide wire,
      (v) an adjustable depth control stop for mounting on and fixing to each of the cannulas to prevent cannula advancement for monitoring its depth into the tissue when in contact with the tissue,
      (vi) an electrosurgical handpiece comprising an elongated member having a proximal end and a distal end and configured to fit within and extend through each of the cannula's lumen with the proximal end of the elongated member remaining outside of the proximal end of a cannula when the distal end has exited the distal end of the cannula, the handpiece having at the distal end of the elongated member an active extendable electrosurgical electrode, the electrosurgical handpiece when energized with RF power generating RF electrosurgical currents at its electrode,
   (b) positioning a patent in a prone position,
   (c) subjecting the patient to conscious sedation,
   (d) a spinal needle with a lumen is inserted into a patient's back 8-10 cm from midline toward a spinal disc comprising an annulus surrounding a nucleus pulposus and through an intervertebral foramen, one of the guide wires is threaded through the needle lumen into the disc nucleus,
   (e) next a 3-4 mm skin incision is made at the needle site and the spinal needle is then removed leaving the guide wire in place,
   (f) next one of the cannulas and the dilator are joined together and are placed over the guide wire and together advanced toward the annulus,
   (g) when an annulotomy is to be performed, next the trephine is inserted into and advanced through the cannula lumen toward the outer surface of the disc annulus and an annulotomy created by applying a slight pressure and rotation of the trephine 1-3 turns followed by removing the trephine and replacing the trephine with the dilator,
   (h) next the cannula with joined dilator is advanced under fluoroscopic guidance into the nucleus,
   (i) next the dilator is removed from the cannula creating a portal into the disc,
   (j) next the depth control stop is mounted on the cannula and advanced to the patient's skin and secured to the cannula to prevent advancement of the cannula,
   (k) next the electrosurgical instrument with the active extendable electrosurgical electrode leading is advanced through the cannula and into the pulposus,
   (l) then the electrosurgical instrument is energized with RF power causing RF electrosurgical currents from the electrosurgical electrode into the pulposus to remove, shrink or modulate pulposus or annulus tissue.

5. A procedure as claimed in claim 4, wherein the electrosurgical handpiece comprises at the proximal end of the elongated member a handle capable when actuated of selectively causing the active electrosurgical electrode to extend from and retract into the elongated member, and wherein the active electrosurgical electrode is bipolar and bendable at the distal end of the elongated member when extended to access tissue non-aligned with the cannula, (m) during step (l) the electrosurgical electrode is deployed and retracted to create tracks of nucleus removal to accomplish nucleus pulposus decompression.

6. A procedure as claimed in claim 5, wherein the elongated member is rigid.

7. A procedure as claimed in claim 5, wherein each of the cannulas has an enlarged head at one end, the enlarged head having an internally threaded opening, and wherein the dilator has an enlarged head at one end, the enlarged head having an externally threaded extension configured to threadingly engage the internally threaded opening on each of the cannula's head, (n) step (f) is carried out by joining the cannula to the dilator by screwing them together.

8. A procedure as claimed in claim 5, wherein the depth control stop comprises two threaded members with diameters exceeding that of the cannula that when tightened lock to the cannula, (o) step (j) is carried out by counter-rotating the two threaded members to lock the depth control stop to the cannula when the depth control stop is against the patient.

9. A procedure as claimed in claim 5, wherein the dilator has a length such that, when fully engaging either of the cannula's lumen, the dilator's end protrudes about 3-5 mm from the end of the cannula, and wherein the trephine has a length such that, when fully engaging each of the cannula's lumen, the trephine's end protrudes up to about 10 mm from the end of the cannula.

10. A procedure as claimed in claim 9, wherein the dilator has a tapered end and the trephine has a cutting end.

11. A procedure as claimed in claim 5, wherein during step (m) the electrosurgical electrode is deployed and retracted to create spaced tracks of nucleus removal.

12. A procedure as claimed in claim 4, further providing an electrosurgical generator generating MHz electrosurgical currents for connection to the electrosurgical handpiece, and energizing the generator to provide the RF electrosurgical currents to the electrosurgical electrode.

* * * * *